(12) United States Patent
Patton

(10) Patent No.: US 10,702,621 B1
(45) Date of Patent: Jul. 7, 2020

(54) DOOR MAT

(71) Applicant: Ricardo Patton, Centennial, CO (US)

(72) Inventor: Ricardo Patton, Centennial, CO (US)

(*) Notice: Subject to any disclaimer, the term of this patent is extended or adjusted under 35 U.S.C. 154(b) by 285 days.

(21) Appl. No.: 15/883,161

(22) Filed: Jan. 30, 2018

(51) Int. Cl.
| | |
|---|---|
| *A61L 2/26* | (2006.01) |
| *B32B 27/08* | (2006.01) |
| *A47L 23/26* | (2006.01) |
| *A61L 2/232* | (2006.01) |
| *B32B 27/30* | (2006.01) |

(52) U.S. Cl.
CPC ............... *A61L 2/26* (2013.01); *A47L 23/266* (2013.01); *A61L 2/232* (2013.01); *B32B 27/08* (2013.01); *B32B 27/306* (2013.01); *B32B 2471/04* (2013.01)

(58) Field of Classification Search
CPC .......... A61L 2/26; A61L 2/232; A47L 23/266; B32B 27/08; B32B 27/306; B32B 2471/04
See application file for complete search history.

(56) References Cited

U.S. PATENT DOCUMENTS

| | | | |
|---|---|---|---|
| 3,696,459 A | 10/1972 | Kucera | |
| 6,258,435 B1 | 7/2001 | Staal | |
| 6,886,210 B2 | 5/2005 | Dean | |
| D666,860 S | 9/2012 | Lubart | |
| 9,451,871 B1 | 9/2016 | Seaberg | |
| 2009/0145459 A1* | 6/2009 | Gonzales | A47L 13/16 134/6 |
| 2009/0229732 A1* | 9/2009 | Determan | B32B 7/12 156/60 |
| 2010/0296970 A1* | 11/2010 | Trimarco | A47K 3/022 422/37 |
| 2015/0330029 A1* | 11/2015 | Ramaratnam | D21H 27/40 15/104.93 |
| 2016/0015844 A1 | 1/2016 | Collins | |
| 2017/0128606 A1 | 5/2017 | Jackson | |

FOREIGN PATENT DOCUMENTS

WO  2016147087  9/2016

* cited by examiner

*Primary Examiner* — Andrew A Horton
(74) *Attorney, Agent, or Firm* — Kyle A. Fletcher, Esq.

(57) ABSTRACT

The door mat is a dry disinfection apparatus. The door mat comprises a pedestal, a sheeting pad, and a disinfecting substance. The disinfecting substance forms a coating on the sheeting pad. The sheeting pad mounts on the pedestal. The door mat is used by having a person step on the sheeting pad of the door mat during the normal walking process. The disinfecting substance chemically reacts with microorganisms found on the exterior surface of the footwear (or foot) placed on the sheeting pad. This chemical reaction mitigates the risk of subsequent contamination.

17 Claims, 4 Drawing Sheets

DOOR MAT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science, more specifically, an apparatus for disinfecting objects other than foodstuffs using a chemical substance.

SUMMARY OF INVENTION

The door mat is a dry disinfection apparatus. The door mat comprises a pedestal, a sheeting pad, and a disinfecting substance. The disinfecting substance forms a coating on the sheeting pad. The sheeting pad mounts on the pedestal. The door mat is used by having a person step on the sheeting pad of the door mat during the normal walking process. The disinfecting substance chemically reacts with microorganisms found on the exterior surface of the footwear (or foot) placed on the sheeting pad. This chemical reaction mitigates the risk of subsequent contamination.

These together with additional objects, features and advantages of the door mat will be readily apparent to those of ordinary skill in the art upon reading the following detailed description of the presently preferred, but nonetheless illustrative, embodiments when taken in conjunction with the accompanying drawings.

In this respect, before explaining the current embodiments of the door mat in detail, it is to be understood that the door mat is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the door mat.

It is therefore important that the claims be regarded as including such equivalent construction insofar as they do not depart from the spirit and scope of the door mat. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
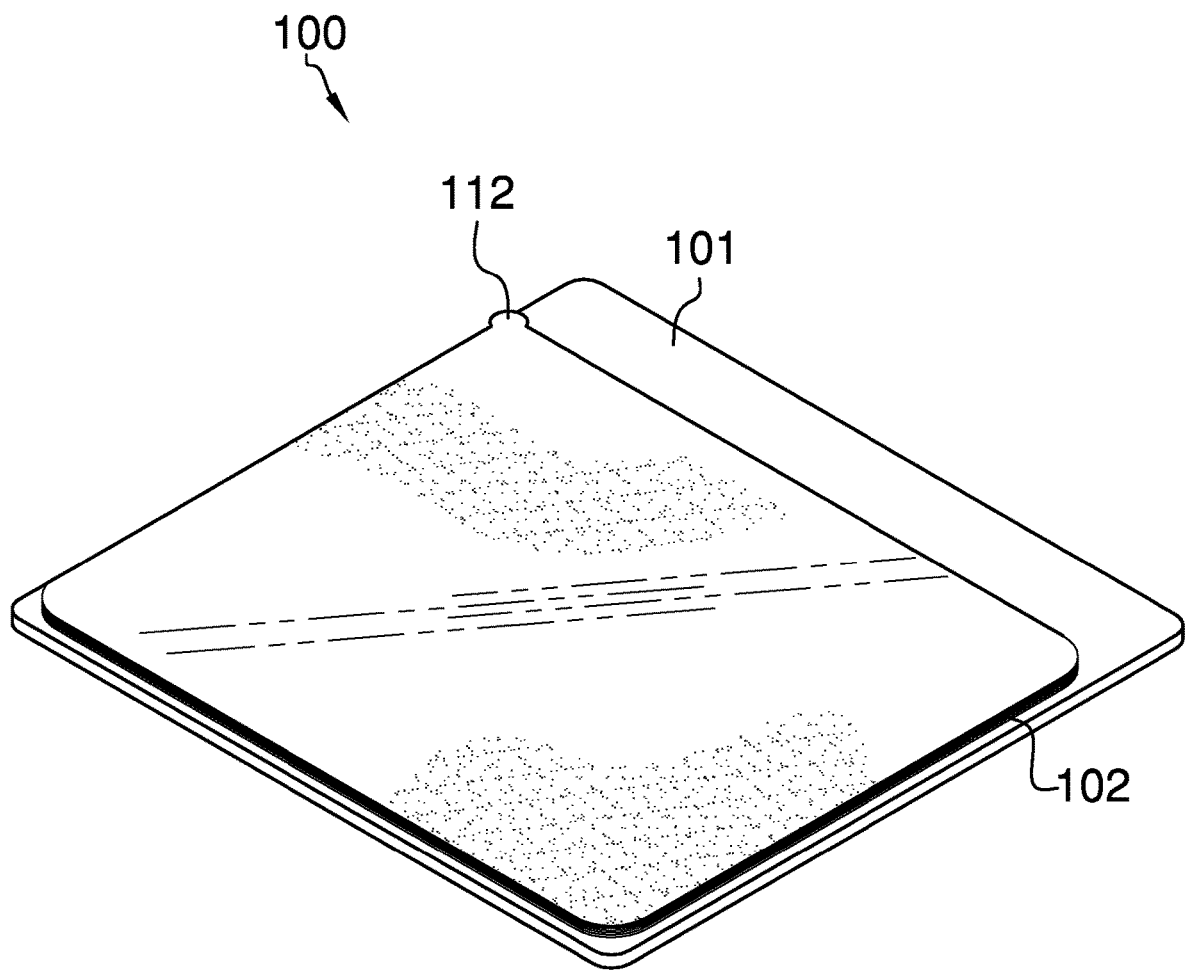
FIG. 1 is a perspective view of an embodiment of the disclosure.
Figure 2:
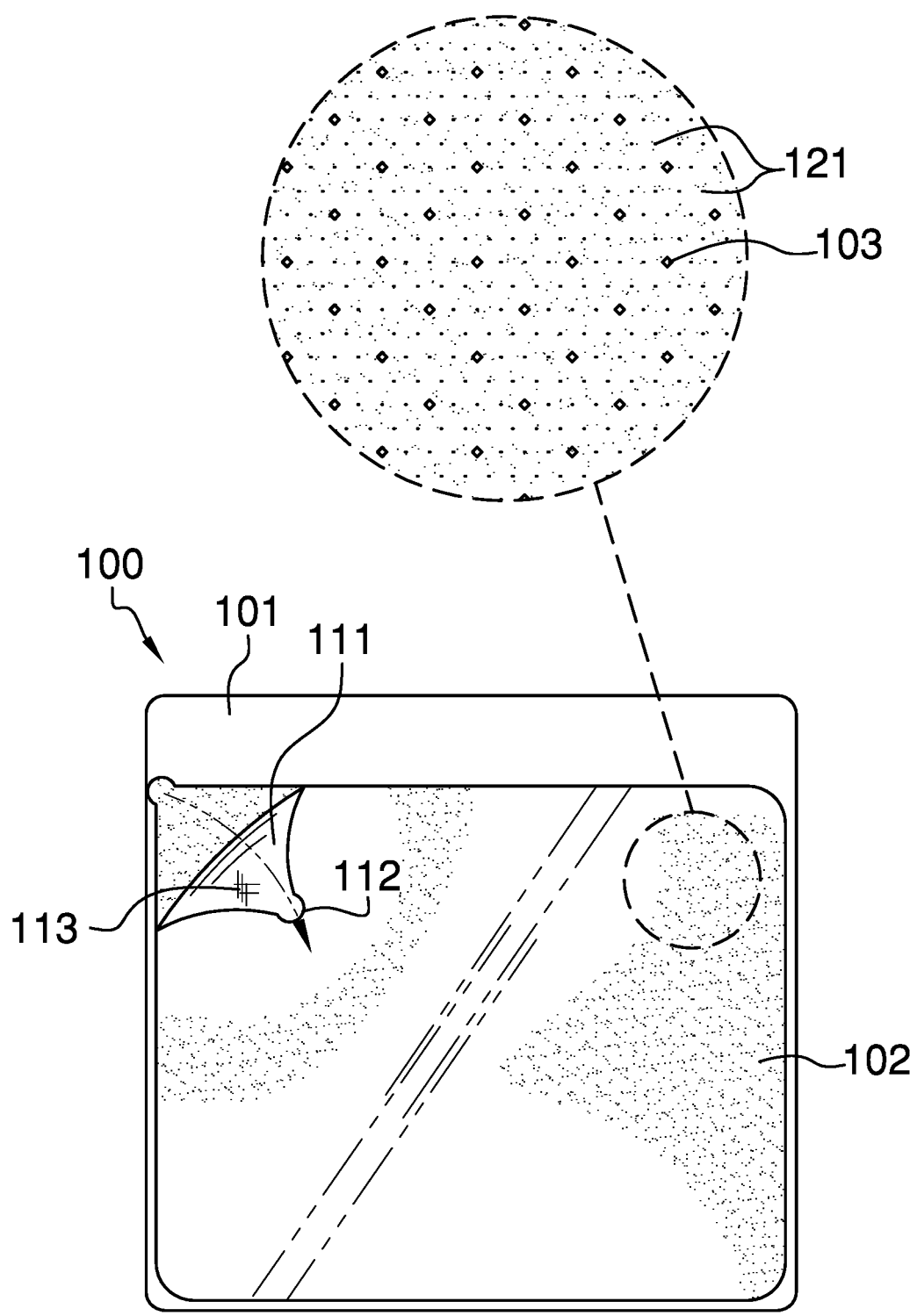
FIG. 2 is a top view of an embodiment of the disclosure.
Figure 3:
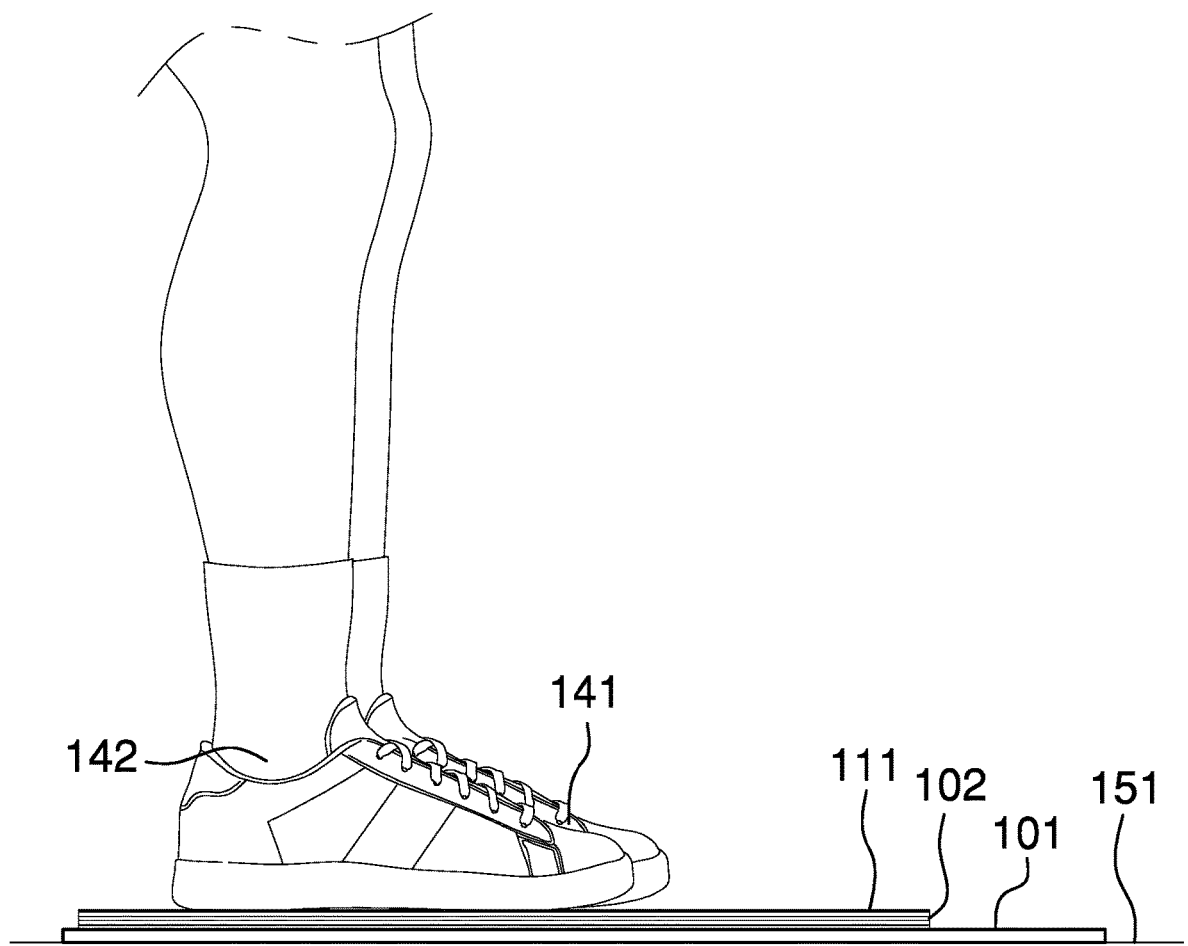
FIG. 3 is an in-use view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 4.

The door mat 100 (hereinafter invention) is a dry disinfection apparatus. The invention 100 is adapted for use with a person. The person is further defined with a footwear 141 and a foot 142. The invention 100 disinfects an item selected from the group consisting of the footwear 141 and the foot 142. The selected item is hereinafter referred to as the footwear 141. The invention 100 comprises a pedestal 101, a sheeting pad 102, and a disinfecting substance 103. The disinfecting substance 103 forms a coating on the sheeting pad 102. The sheeting pad 102 mounts on the pedestal 101. The invention 100 is used by having a person step on the sheeting pad 102 of the invention 100 during the normal walking process. The disinfecting substance 103 chemically reacts with microorganisms found on the exterior surface of the footwear 141 (or foot 142) placed on the sheeting pad 102. This chemical reaction mitigates the risk of subsequent contamination.

The pedestal 101 is a rectangular block structure. The pedestal 101 forms an intermediate structure between the sheeting pad 102 and a supporting surface 151. The pedestal 101 provides a stable raised platform upon which the foot 142 is placed to disinfect the footwear 141.

The sheeting pad 102 is a pad formed from a plurality of stacked individual sheets 111. Each individual sheet 111 of the sheeting pad 102 is coated with a disinfecting substance 103. When the footwear 141 is placed on an individual sheet 111, the disinfecting substance 103 coating the individual sheet 111 comes in direct contact with the footwear 141. The direct contact of the disinfecting substance 103 on the footwear 141 disinfects the footwear 141 reducing the potential risk of contamination by the footwear 141. The sheeting pad 102 comprises a collection of individual sheets 111.

The individual sheet 111 is formed from a sheeting made of polyvinyl acetate 121. The polyvinyl acetate 121 is further defined with a plurality of monomers formed from a vinyl group 122, and an acetate that is further defined with a carboxyl group 123. The polyvinyl acetate 121 is discussed in greater detail elsewhere in this disclosure. The vinyl group 122 of the polyvinyl acetate 121 is discussed in greater detail elsewhere in this disclosure. The carboxyl group 123 of the polyvinyl acetate 121 is discussed in greater detail elsewhere in this disclosure.

The individual sheets 111 are cut after they have been coated with the disinfecting substance 103. Each individual sheet 111 contained in the sheeting pad 102 is formed from the sheeting material. The individual sheet 111 further comprises a grip disk 112 and an adhesive 113. The sheeting material is cut into a rectangular shape with a grip disk 112 formed at a vertex. The grip disk 112 is a circular structure that allows a person to grip the individual sheet 111. The grip disk 112 allows a person to peel an individual sheet 111 off the sheeting pad 102. The individual sheet 111 is peeled off the sheeting pad 102 to provide access to a fresh coating of disinfecting substance 103 on a new individual sheet 111.

The adhesive 113 is a removable adhesive 113 applied to the side of each individual sheet 111 that is proximal to the pedestal 101. The function of the adhesive 113 is to: 1) prevent the top individual sheet 111 from slipping when stepped on; and, 2) to protect the disinfecting substance 103 applied to the individual sheet 111 from oxidation and hydration reactions while being stored on the sheeting pad 102.

The disinfecting substance 103 is a dry compound that is applied to the individual sheet 111 as a coating. The disinfecting substance 103 is a commercially available product. In the first potential embodiment of the disclosure, the sheeting material is formed from polyvinyl acetate 121. Each molecule of disinfecting substance 103 binds to the polyvinyl acetate 121 of an individual sheet 111 using a hydrogen bond 133.

The following two paragraphs describe the application of the disinfecting substance 103 to the individual sheet 111 and the application of the disinfecting substance 103 to the footwear 141.

The disinfecting substance 103 is dissolved into a solvent selected from the group consisting of water and alcohol. The selected solvent is used to form a disinfecting substance 103 solution. The applicant prefers the use of an alcohol solution because of the higher volatility of alcohol relative to water. The individual sheet 111 is submerged into the disinfecting substance 103 solution. The solvent used in the disinfecting substance 103 solution is then evaporated off the individual sheet 111. During the evaporation process, each disinfecting substance 103 molecule forms a hydrogen bond 133 with the carboxyl group 123 of the polyvinyl acetate 121 that forms the individual sheet 111.

The frictional forces of sliding the footwear 141 along the individual sheet 111 are enough to release the hydrogen bond 133 joining the carboxyl group 123 to the disinfecting substance 103 thereby applying the disinfecting substance 103 to the footwear 141.

In the first potential embodiment of the disclosure, the disinfecting substance 103 is selected from the group consisting of sodium dichloroisocyanurate 131 (CAS 2893-78-9) and sodium dichloroisocyanurate dihydrate 132 (CAS 51580-86-0).

The selection between sodium dichloroisocyanurate 131 (CAS 2893-78-9) and the sodium dichloroisocyanurate dihydrate 132 (CAS 51580-86-0) comprises a manufacturing tradeoff that is not critical to either the presented innovation of or to the efficacy of disinfection provided by the disclosure. The use of the sodium dichloroisocyanurate 131 (CAS 2893-78-9) offers more bonding sites for hydrogen bonding 133 with the carboxyl group of the polyvinyl acetate 121 during the coating process which results in a better yield of sodium dichloroisocyanurate 131 (CAS 2893-78-9) on the individual sheet 111 after processing. The use of sodium dichloroisocyanurate dihydrate 132 (CAS 51580-86-0) results in a more shelf stable product. Specifically, the sodium dichloroisocyanurate dihydrate 132 (CAS 51580-86-0) is less susceptible to oxidation and hydration reactions during storage of the invention 100.

Figure 4:
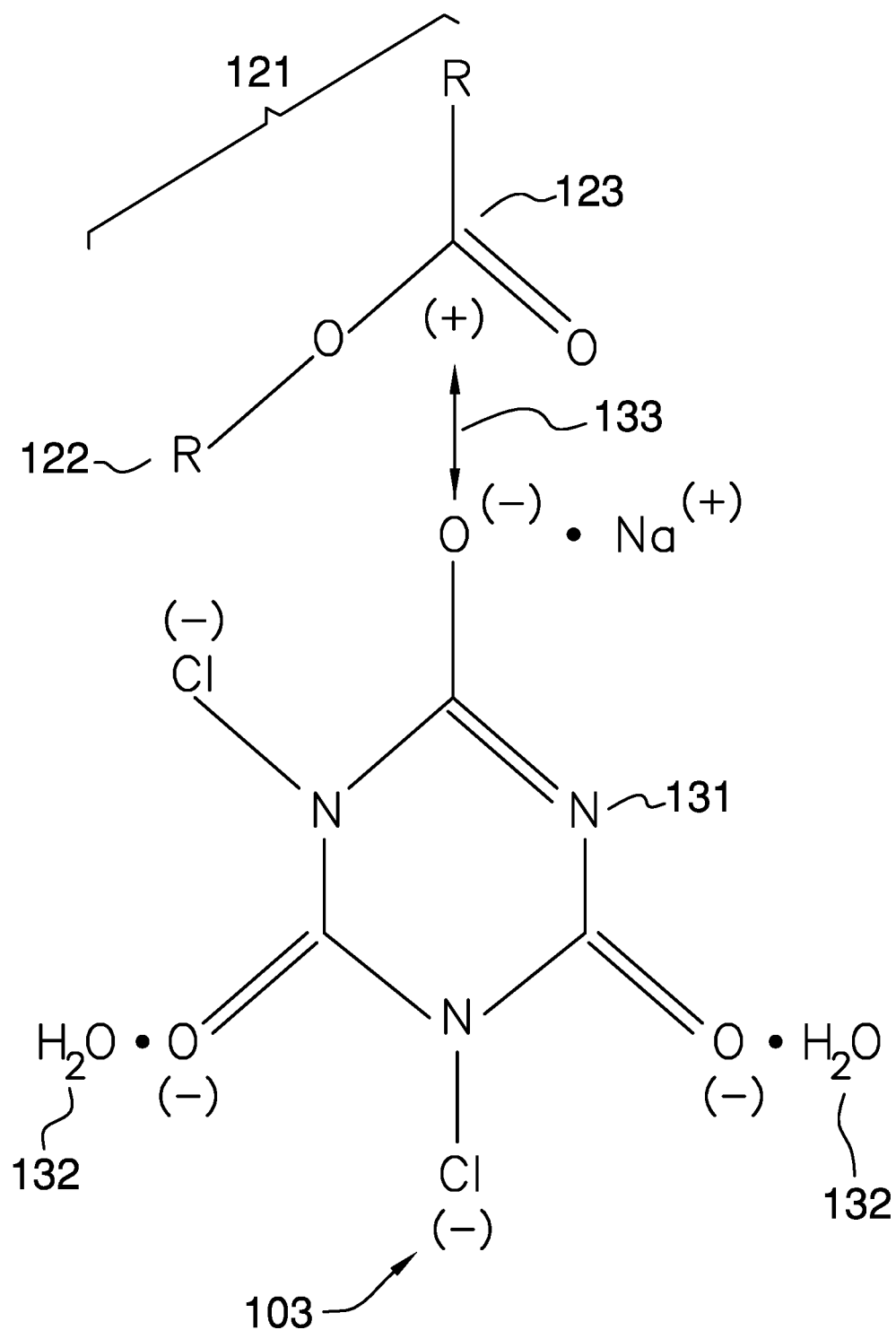
FIG. 4 is a detail view of an embodiment of the disclosure.

As shown most clearly in FIG. 4, the applicant hypothesizes that the negative bond of the anhydrate oxygen atom of the sodium dichloroisocyanurate 131 (CAS 2893-78-9) forms the hydrogen bond 133 with the carboxyl group 123 of the polyvinyl acetate 121. The hydrogen bond 133 is an electrostatic interaction between cation of a first molecule and the anion of a second molecule. The low bond energy of the hydrogen bond 133 allows the sodium dichloroisocyanurate 131 (CAS 2893-78-9) to be readily removed by the friction of the footwear 141. The hydrogen bond 133 is discussed in greater detail elsewhere in this disclosure.

The sodium dichloroisocyanurate 131 (CAS 2893-78-9) and the sodium dichloroisocyanurate dihydrate 132 (CAS 51580-86-0) (hereinafter sodium dichloroisocyanurate 131 (CAS 2893-78-9)) are commercially available disinfectants that are available in powdered form.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Anion: As used in this disclosure, an anion refers to a negatively charged ion.

Carboxyl Functional Group: As used in this disclosure, the carboxyl functional group is a functional group with the chemical formula —COOH.

Cation: As used in this disclosure, a cation refers to a positively charged ion.

Disinfectant: As used in this disclosure, a disinfectant is a chemical that destroys or inhibits the activities of pathogenic microorganisms.

Functional Group: As used in this disclosure, a functional group is specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkenes, haloalkynes, and ketones. As a practical matter, this definition intends to use the term functional group in the same manner as the term is commonly used in organic chemistry.

Grip: As used in this disclosure, a grip is an accommodation formed on or within an object that allows the object to be grasped or manipulated by a hand.

Halogen: As used in this disclosure, a halogen refers to a chemical element found in column 17 of the periodic table.

Hydrogen Bond: As used in this disclosure, a hydrogen bond refers to an electrostatic attraction between: 1) a cation and an anion; 2) a cation and a negative dipole; or, 3) anion and a positive dipole. The exchange of electrons (as would occur in an ionic bond or covalent bond) does not occur in a hydrogen bond. As a rule, the energy to break an ionic bond is less than the energy required to break a covalent bond or an ionic bond.

Load Path: As used in this disclosure, a load path refers to a chain of one or more structures that transfers a load generated by a raised structure or object to a foundation, supporting surface, or the earth.

Microorganism: As used in this disclosure, a microorganism is an organism too small to be viewed by the unaided eye. Microorganisms are typically single-celled organisms such as bacteria, yeast, viruses, protozoa, fungi, and algae.

Pad: As used in this disclosure, a pad is a stack of individual sheets of a sheeting material. Pads are often assembled to allow for the distribution of individual sheets.

Pedestal: As used in this disclosure, a pedestal is an intermediary load bearing structure that that transfers a load path between a supporting surface and an object, structure, or load.

Polymer: As used in this disclosure, a polymer refers to a molecular chain that comprises multiple repeating units known as monomers. The repeating unit may be an atom or a molecular structure.

Removable Adhesive: As used in this disclosure, a removable adhesive is a commercially available adhesive that is designed with a lower tack, or stickiness, such that a first object is attached to a second object with a removable adhesive the first object can be readily removed in a manner that ideally, though not necessarily practically, leaves behind no adhesive residue on the second object. A repositionable adhesive is a subset of removable adhesives that are intended to allow the first object to be reattached to a third object or the second object in the initial or a different position. Within this disclosure, a removable adhesive is assumed to include repositionable adhesives.

Sheeting: As used in this disclosure, a sheeting is a material, such as a textile, a plastic, or a metal foil, in the form of a thin flexible layer or layers.

Sodium Dichloroisocyanurate: As used in this disclosure, sodium dichloroisocyanurate is a commonly used name for sodium 3,5-dichloro-2,4,6-trioxy,1,3,5-triazinan-1-ide (CAS 2893-78-9). Sodium dichloroisocyanurate is a commonly used disinfecting agent that is available in a powder form. Sodium dichloroisocyanurate is soluble in water and alcohol. Sodium dichloroisocyanurate is also available in a dihydride formulation (sodium dichloroisocyanurate hydride CAS: 51580-86-0).

Supporting Surface: As used in this disclosure, a supporting surface is a horizontal surface upon which an object is placed and to which the load path of the object is transferred. This disclosure assumes that an object placed on the supporting surface is in an orientation that is appropriate for the normal or anticipated use of the object.

Vinyl: As used in this disclosure, a vinyl refers to a chemical structure with a form RHC=CH2. In this structure, the R refers to a chemical substance including, but not limited to, a functional group, a halide, and a hydrogen atom. A polymer is often formed from vinyl monomers by breaking the double bond between the carbon atoms in a manner that forms a chain of vinyl monomers linked by single bonded carbon atoms.

Vinyl Acetate: As used in this disclosure, a vinyl acetate (CAS 108-05-04) refers to a vinyl molecule where the R group is formed from acetate (CH3CO2 CAS 71-50-01). The acetate attaches to the vinyl as an ester which attaches a carboxyl functional group to the vinyl.

The following definition was used in this disclosure:
The following definitions and directional references were used in this disclosure:

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An apparatus for disinfecting footwear comprising:
a pedestal, a sheeting pad, and a disinfecting substance;
wherein the disinfecting substance forms a coating on the sheeting pad;
wherein the sheeting pad mounts on the pedestal;
wherein the apparatus for disinfecting footwear is a dry disinfection apparatus;
wherein the apparatus for disinfecting footwear is adapted for use with a person;
wherein the person is further defined with a footwear and a foot;
wherein the apparatus for disinfecting footwear disinfects an item selected from the group consisting of the footwear and the foot;
wherein the selected item is hereinafter referred to as the footwear;
wherein the sheeting pad is a pad formed from a plurality of stacked individual sheets;
wherein each individual sheet of the sheeting pad is coated with a disinfecting substance;
wherein each individual sheet is formed from a polyvinyl acetate;
wherein the disinfecting substance is a dry compound;
wherein each molecule of disinfecting substance binds to the polyvinyl acetate of an individual sheet using a hydrogen bond.

2. The apparatus for disinfecting footwear according to claim 1
wherein the person steps on the sheeting pad;
wherein the disinfecting substance chemically reacts with microorganisms found on the exterior surface of the footwear.

3. The apparatus for disinfecting footwear according to claim 2
wherein the pedestal is a rectangular block structure;
wherein the pedestal forms an intermediate structure between the sheeting pad and a supporting surface.

4. The apparatus for disinfecting footwear according to claim 3 wherein the disinfecting substance on the individual sheet comes in direct contact with the footwear.

5. The apparatus for disinfecting footwear according to claim 4
wherein the polyvinyl acetate is further defined with a plurality of monomers formed from a vinyl group and an acetate;
wherein the acetate is further defined with a carboxyl group.

6. The apparatus for disinfecting footwear according to claim 5 wherein the individual sheets are cut after having been coated with the disinfecting substance.

7. The apparatus for disinfecting footwear according to claim 6
wherein each individual sheet further comprises a grip disk and an adhesive;
wherein the sheeting material is cut into a rectangular shape with the grip disk formed at a vertex;
wherein the grip disk is a circular structure;
wherein the adhesive is a removable adhesive applied to the side of each individual sheet that is proximal to the pedestal.

8. The apparatus for disinfecting footwear according to claim 7 wherein the frictional forces of sliding the footwear along the individual sheet are enough to release the hydrogen bond joining the carboxyl group to the disinfecting substance.

9. The apparatus for disinfecting footwear according to claim 8
wherein the disinfecting substance is selected from the group consisting of sodium dichloroisocyanurate (CAS 2893-78-9) and sodium dichloroisocyanurate dihydrate (CAS 51580-86-0);
wherein the negative bond of the anhydrate oxygen atom of the sodium dichloroisocyanurate (CAS 2893-78-9) forms the hydrogen bond with the carboxyl group of the polyvinyl acetate.

10. An apparatus for disinfecting footwear comprising:
a pedestal, a sheeting pad, and a disinfecting substance;
wherein the disinfecting substance forms a coating on the sheeting pad;
wherein the sheeting pad mounts on the pedestal;
wherein the apparatus for disinfecting footwear is a dry disinfection apparatus;
wherein the apparatus for disinfecting footwear is adapted for use with a person;
wherein the person is further defined with a footwear and a foot;
wherein the apparatus for disinfecting footwear disinfects an item selected from the group consisting of the footwear and the foot;
wherein the selected item is hereinafter referred to as the footwear;
wherein the disinfecting substance is selected from the group consisting of sodium dichloroisocyanurate (CAS 2893-78-9) and sodium dichloroisocyanurate dihydrate (CAS 51580-86-0);
wherein the disinfecting substance is bonded to the sheeting material using a hydrogen bond;
wherein the disinfecting substance is a dry compound;
wherein each molecule of disinfecting substance binds to the polyvinyl acetate of an individual sheet using the hydrogen bond.

11. The apparatus for disinfecting footwear according to claim 10
wherein the person steps on the sheeting pad;
wherein the disinfecting substance chemically reacts with microorganisms found on the exterior surface of the footwear.

12. The apparatus for disinfecting footwear according to claim 11
wherein the pedestal is a rectangular block structure;
wherein the pedestal forms an intermediate structure between the sheeting pad and a supporting surface;
wherein the sheeting pad is a pad formed from a plurality of stacked individual sheets;
wherein each individual sheet of the sheeting pad is coated with a disinfecting substance.

13. The apparatus for disinfecting footwear according to claim 12 wherein the disinfecting substance on the individual sheet comes in direct contact with the footwear.

14. The apparatus for disinfecting footwear according to claim 13
wherein each individual sheet is formed from a polyvinyl acetate;
wherein the polyvinyl acetate is further defined with a plurality of monomers formed from a vinyl group and an acetate;
wherein the acetate is further defined with a carboxyl group.

15. The apparatus for disinfecting footwear according to claim 14 wherein the individual sheets are cut after having been coated with the disinfecting substance.

16. The apparatus for disinfecting footwear according to claim 15
wherein each individual sheet further comprises a grip disk and an adhesive;
wherein the sheeting material is cut into a rectangular shape with the grip disk formed at a vertex;
wherein the grip disk is a circular structure;
wherein the adhesive is a removable adhesive applied to the side of each individual sheet that is proximal to the pedestal.

17. The apparatus for disinfecting footwear according to claim 16 wherein the frictional forces of sliding the footwear along the individual sheet release the hydrogen bond joining the carboxyl group to the disinfecting substance.

* * * * *